United States Patent
Kim et al.

(10) Patent No.: US 9,963,017 B2
(45) Date of Patent: May 8, 2018

(54) AIR CONDITIONER FOR VEHICLE WITH PHOTOCATALYTIC MODULE

(71) Applicant: HANON SYSTEMS, Daejeon (KR)

(72) Inventors: Jae Ho Kim, Daejeon (KR); Sung Je Lee, Daejeon (KR); Hyung Joo Kim, Daejeon (KR)

(73) Assignee: HANON SYSTEMS, Daejeon (KR)

( * ) Notice: Subject to any disclaimer, the term of this patent is extended or adjusted under 35 U.S.C. 154(b) by 0 days. days.

(21) Appl. No.: 14/907,602

(22) PCT Filed: Jan. 27, 2015

(86) PCT No.: PCT/KR2015/000824
§ 371 (c)(1),
(2) Date: Jan. 26, 2016

(87) PCT Pub. No.: WO2015/167110
PCT Pub. Date: Nov. 5, 2015

(65) Prior Publication Data
US 2017/0036516 A1   Feb. 9, 2017

(30) Foreign Application Priority Data

Apr. 30, 2014  (KR) .................. 10-2014-0052076
Apr. 30, 2014  (KR) .................. 10-2014-0052080

(51) Int. Cl.
*B60H 3/00* (2006.01)
*B60H 3/06* (2006.01)
(Continued)

(52) U.S. Cl.
CPC ............... *B60H 3/00* (2013.01); *A61L 9/205* (2013.01); *B60H 1/12* (2013.01); *B60H 3/0658* (2013.01); *B60H 2003/0675* (2013.01)

(58) Field of Classification Search
CPC .......... B60H 3/00; B60H 1/12; B60H 3/0658; B60H 2003/0675; A61L 9/205; A61L 9/00; A61L 2/00; A61L 9/20
See application file for complete search history.

(56) References Cited

U.S. PATENT DOCUMENTS 6,468,491 B1 * 10/2002 Foury ..................... B60H 3/06
                                                     180/90
8,658,101 B1 *  2/2014 Burnett ................. B01J 35/004
                                                     422/121
(Continued)

FOREIGN PATENT DOCUMENTS

JP        5-104946 A      4/1993
JP        H05104946 A     4/1993
(Continued)

OTHER PUBLICATIONS

International Search Report dated Apr. 28, 2015 from corresponding International Patent Application Serial No. PCT/KR2015/000824.

*Primary Examiner* — Emmanuel Duke
(74) *Attorney, Agent, or Firm* — Dickinson Wright PLLC

(57) ABSTRACT

An air conditioner for a vehicle with a photocatalytic module, which can purify air introduced into the inside of an air-conditioning case, sterilize and deodorize an evaporator and provide an optimized installation position of a photocatalytic module so that the photocatalytic module can be easily attached and detached and conveniently maintained and repaired. The air conditioner includes an air-conditioning case having an air inflow port, air outflow ports, an air passageway formed inside the air-conditioning case, an evaporator mounted on an air passageway of the air-conditioning case, an air blower for blowing inside air of the air-conditioning case, and a photocatalytic module disposed at one side of the air-conditioning case. The photocatalytic module includes a catalyst part which causes a photocata- (Continued)

lytic reaction by irradiated light to generate radicals and at least one light source part for irradiating UV light toward the catalyst part.

23 Claims, 19 Drawing Sheets

(51) Int. Cl.
*A61L 9/20* (2006.01)
*B60H 1/12* (2006.01)

(56) References Cited

U.S. PATENT DOCUMENTS

| | | | | |
|---|---|---|---|---|
| 8,911,670 | B2* | 12/2014 | Wang | B01D 53/8668 422/120 |
| 9,205,169 | B1* | 12/2015 | Burnett | A61L 2/20 |
| 2003/0021720 | A1* | 1/2003 | Reisfeld | A61L 9/20 422/4 |
| 2004/0170537 | A1* | 9/2004 | Hara | A61L 9/014 422/122 |
| 2009/0263298 | A1* | 10/2009 | Hsu | B01J 19/123 422/186.3 |
| 2010/0135864 | A1* | 6/2010 | Taniguchi | A61L 9/18 422/121 |
| 2013/0034470 | A1* | 2/2013 | Wang | B01D 53/8668 422/121 |

FOREIGN PATENT DOCUMENTS

| | | |
|---|---|---|
| JP | 9-066096 A | 3/1997 |
| JP | H0966096 A | 3/1997 |
| JP | 2549032 U | 5/1997 |
| JP | H10244829 A | 9/1998 |
| JP | 2001-163032 A | 6/2001 |
| JP | 2001171343 A | 6/2001 |
| JP | 2003070885 A | 3/2003 |
| JP | 2004100585 A | 4/2004 |
| JP | 2012017006 A | 1/2012 |
| JP | 2012158320 A | 8/2012 |
| KR | 2002-0058680 A | 7/2002 |
| KR | 20020058680 A | 7/2002 |
| KR | 20080030325 A | 4/2008 |
| KR | 10-1275522 B1 | 6/2013 |

* cited by examiner

PRIOR ART

| Division Microbial content (removal rate) | | Measurement position_front face part of evaporator | | | | |
|---|---|---|---|---|---|---|
| | | front face1 | front face2 | front face3 | front face4 | front face5 |
| Mounting position | Blank | 262 | 258 | 312 | 342 | 292 |
| | P1 | 87(67%) | 70(73%) | 53(83%) | 142(58%) | 164(44%) |
| | P2 | 56(79%) | 55(79%) | 89(71%) | 133(61%) | 78(73%) |
| | P3 | 37(86%) | 42(84%) | 31(90%) | 50(85%) | 115(60%) |
| | P4 | 24(91%) | 8(97%) | 9(97%) | 33(90%) | 74(75%) |
| Remark | | Blank:Microbial content after one-hour operation of blower after bacteria inoculation(At the time of non-operation of UV module) | | | | |

AIR CONDITIONER FOR VEHICLE WITH PHOTOCATALYTIC MODULE

CROSS-REFERENCE TO RELATED APPLICATIONS

This application is a National Stage of International Application No. PCT/KR2015/000824, filed Jan. 27, 2015, which claims the benefit and priority of KR 10-2014-0052076 filed Apr. 30, 2014 and KR 10-2014-0052080 filed Apr. 30, 2014. The entire disclosures of each of the above applications are incorporated herein by reference.

TECHNICAL FIELD

The present invention relates to an air conditioner for a vehicle with a photocatalytic module, and more particularly, to an air conditioner for a vehicle with a photocatalytic module which can purify air flown into an air-conditioning case and sterilize and deodorize an evaporator.

BACKGROUND ART

In general, an air conditioner for a vehicle is a device for heating or cooling air by introducing outside air indoors or circulating inside air to heat or cool the inside of the vehicle. That is, the air conditioner for the vehicle introduces air to the inside of the vehicle by an air blower so that the introduced air passes an evaporator in which refrigerant flows and selectively passes a heater core according to opening and closing of a temperature door so as to selectively blow air to parts of the inside of the vehicle by the door.

According to independent structures of a blower unit, an evaporator unit and a heater core unit, such an air conditioner is classified into a three-piece type air conditioner in which the blower unit, the evaporator unit and the heater core unit are disposed independently, a semi-center type air conditioner in which the evaporator unit and the heater core unit are embedded in the air-conditioning case and the blower unit is mounted separately, and a center-mounting type air conditioner in which the three units are all embedded in the air-conditioning case.

Japanese Patent Publication No. 2549032 (May 30, 1997) discloses a cooling device for a vehicle with a deodorizer. FIG. 1 is a sectional view of a cooling device for a vehicle with a deodorizer according to the prior art.

As shown in FIG. 1, the cooling device for the vehicle with the deodorizer includes: a case 20 having an outside air intake duct 21 and an inside air intake duct 22: and an intake door 23 disposed to be able to rotate to selectively open and close the outside air intake duct 21 and the inside air intake duct 22. An actuator 30 is connected to a rotary shaft of the intake door 23 so as to be controlled by a controller 31.

An air blower 25 is mounted at the downstream side of the intake door 23 to blow the air introduced from the outside air intake duct 21 and the inside air intake duct 22 to the downstream side. The air blower 25 includes a fan 32 and a motor 33 for rotating the fan 32. An evaporator 26 is mounted at the downstream side in the air blower 25 and exchanges heat with air passing the evaporator 26 to cool the air. A photocatalytic filter 27 is mounted on an air passageway 28 of the downstream side of the evaporator 26 to generate active oxygen by irradiation of light with long wavelength.

The photocatalytic filter 27 generates active oxygen by irradiation of an ultraviolet lamp 29 so that the active oxygen oxidizes and decomposes ill-smelling materials into oxidized compound of extremely low concentration. The ultraviolet lamp 29 is arranged between the evaporator 26 and the photocatalytic filter 27. A metal catalyst filter 34 is mounted at the downstream side of the photocatalytic filter 27 in order to remove ozone contained in moving air. The unexplained reference numeral 35 designates a temperature sensor, 36 designates a sensor for sensing the level of bad smell, 37 designates a fan switch, and 24 designates an air outlet.

However, the conventional cooling device for the vehicle with the deodorizer has a disadvantage in that the ultraviolet lamp 29 used as a light source for photocatalysis contains mercury therein and mercury is harmful for human bodies and cannot be applied to vehicles due to various environmental conditions. Moreover, the conventional cooling device for the vehicle with the deodorizer has another disadvantage in that the photocatalytic filter 27 mounted at the downstream side of the evaporator 26 must be replaced with a new one due to decrease of air volume when there is excessive dust quantity because it adsorbs and deodorizes bad smells generated from the evaporator 26.

Furthermore, the conventional cooling device for the vehicle with the deodorizer has a further disadvantage in that the deodorizer increases noise and is deteriorated in deodorizing and sterilizing functions and air-conditioning performance because it acts as a resistor of the moving air according to the installation position.

Additionally, the conventional cooling device for the vehicle with the deodorizer has a still further disadvantage in that the deodorizer is generally low in sterilization and deodorization efficiency of the evaporator and in that the deodorizer cannot concentrically sterilize and deodorize parts of the evaporator which are vulnerable to bacteria and bad smell.

DISCLOSURE

Technical Problem

Accordingly, the present invention has been made in an effort to solve the above-mentioned problems occurring in the prior arts, and it is an object of the present invention to provide an air conditioner for a vehicle with a photocatalytic module, which can purify air introduced into the inside of an air-conditioning case, sterilize and deodorize an evaporator and provide an optimized installation position of a photocatalytic module so that the photocatalytic module can be easily attached and detached and conveniently maintained and repaired.

It is another object of the present invention to provide an air conditioner for a vehicle with a photocatalytic module which can minimize resistance of the photocatalytic module to moving air so as to minimize loss of air volume and solve noise problem.

It is a further object of the present invention to provide an air conditioner for a vehicle with a photocatalytic module which can optimize an installation position of the photocatalytic module and an arranged structure between the photocatalytic module and the evaporator to maximize sterilization and deodorization effects.

Technical Solution

To achieve the above objects, the present invention provides an air conditioner for a vehicle with a photocatalytic module including: an air-conditioning case having an air inflow port formed at an entrance side, air outflow ports formed at an exit side and an air passageway formed inside the air-conditioning case; an evaporator mounted on an air passageway of the air-conditioning case; an air blower for blowing inside air of the air-conditioning case; and a photocatalytic module disposed at one side of the air-conditioning case, wherein the photocatalytic module includes: a catalyst part which causes photocatalytic reaction by irradiated light to generate radicals; and at least one light source part for irradiating UV light toward the catalyst part.

According to the present invention, the catalyst part and the light source part are arranged oppositely to inside air and outside air inlets of the air blower in the air flow direction.

According to the present invention, the air conditioner is a rear air conditioner in which the air blower and the evaporator are formed integrally inside the air-conditioning case and is mounted at the rear seat of the vehicle. The catalyst part and the light source part are arranged adjacent to the evaporator than blast fan on the passageway which passes a cutoff of the air blower in the air flow direction.

Advantageous Effects

The air conditioner for the vehicle with the photocatalytic module according to the present invention can prevent decrease of air volume by optimizing the installation structure of the photocatalytic module, use the photocatalytic module semipermanently by selecting kinds of carriers or through a proper on-off control of the light source part, purify air introduced into the inside of an air-conditioning case, sterilize and deodorize the evaporator and provide an optimized installation position of a photocatalytic module so that the photocatalytic module can be easily attached and detached and conveniently maintained and repaired.

Moreover, the air conditioner for the vehicle with the photocatalytic module according to the present invention can increase volume of the air passing the catalyst part by optimizing the installation position of the catalytic module to maximize sterilization and deodorization effects, and minimize resistance of moving air to solve noise problem.

Furthermore, the air conditioner for the vehicle with the photocatalytic module according to the present invention concentrically generates radical to the lower end of the evaporator and concentrates condensate water at the lower part to maximize performance of the photocatalytic module.

MODE FOR INVENTION

Reference will be now made in detail to the preferred embodiment of the present invention with reference to the attached drawings.

Figure 1:
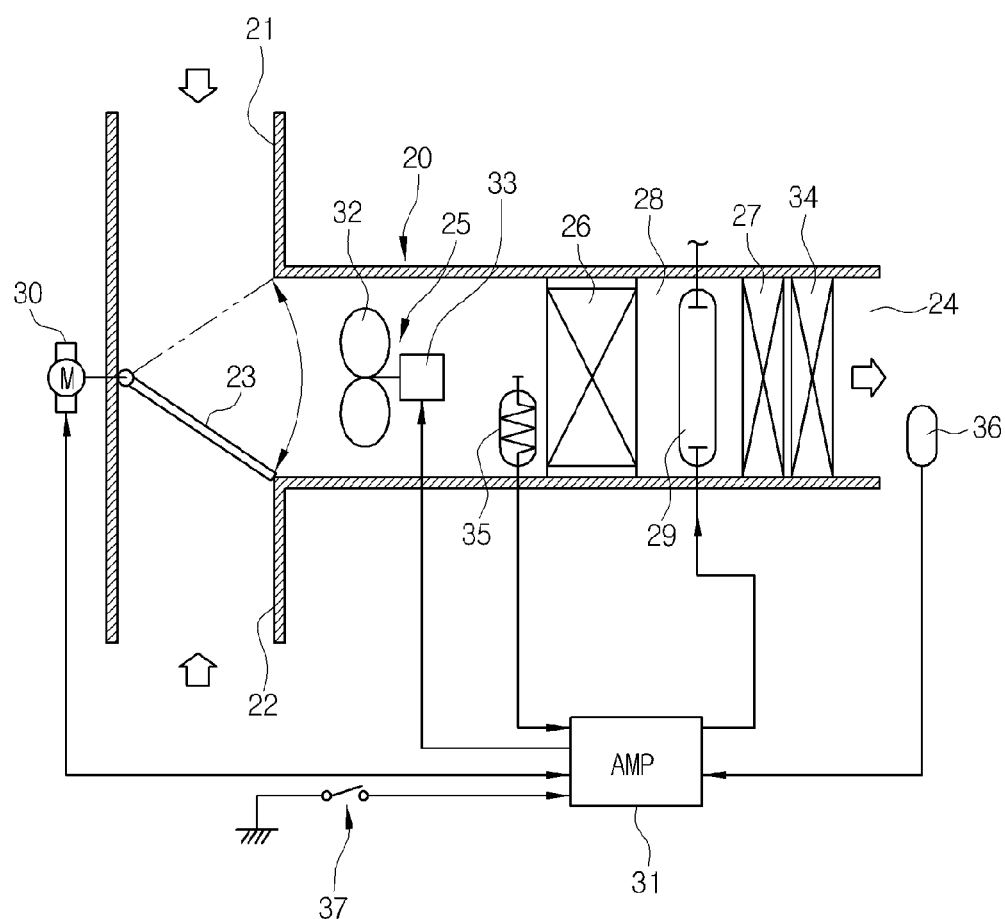
FIG. 1 is a sectional view of a cooling device for a vehicle with a deodorizer according to a prior art.
Figure 2:
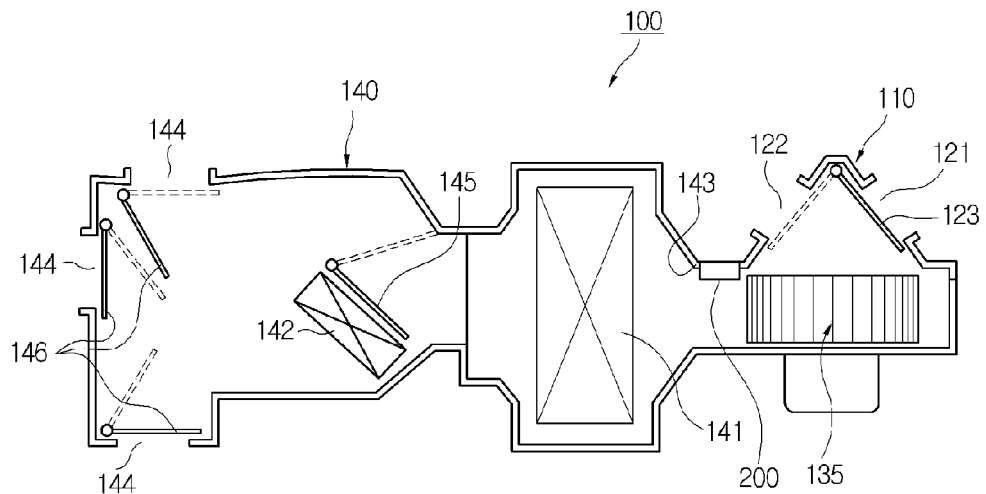
FIG. 2 is a sectional view show a schematic configuration of an air conditioner for a vehicle according to a first preferred embodiment of the present invention.
Figure 3:
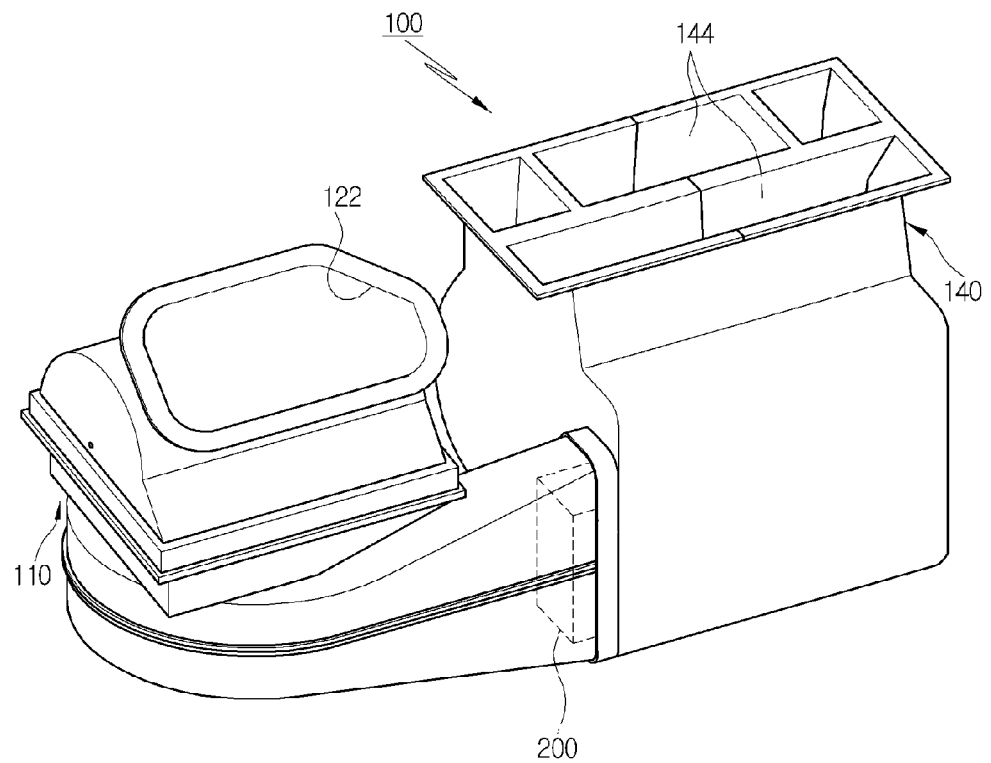
FIG. 3 is a perspective view of the air conditioner for the vehicle according to the first preferred embodiment of the present invention.

FIG. 2 is a sectional view show a schematic configuration of an air conditioner for a vehicle according to a first preferred embodiment of the present invention, and FIG. 3 is a perspective view of the air conditioner for the vehicle according to the first preferred embodiment of the present invention.

As shown in FIGS. 2 and 3, the air conditioner 100 for the vehicle according to the first preferred embodiment of the present invention is a semi-center type air conditioner and includes an air-conditioning case 140, an evaporator 141, a heater core 142, an air blower 110, a temperature-adjusting door 145, a plurality of mode doors 146 and a photocatalytic module 200.

The air-conditioning case 140 includes: an air inflow port 143 formed at an entrance side; a plurality of air outflow ports 144 formed at an exit side; and an air passageway formed inside the air-conditioning case. The evaporator 141 and the heater core 142 are mounted on the air passageway of the air-conditioning case 140 in order and are spaced apart from each other at regular interval. The evaporator 141 exchanges heat with the air flowing in the air passageway to cool the air, and the heater core 142 exchanges heat with the air flowing in the air passageway to heat the air.

The air blower 110 blows inside air air-conditioning case 140, and includes: an inside air inlet 121 and an outside air inlet 122 formed at one side thereof; and an inside and outside air converting door 123 for selectively opening and closing the inside air inlet 121 and the outside air inlet 122. Additionally, the air blower 110 includes a blast fan 135 for forcedly blowing inside air or outside air toward the air inflow port 143 of the air-conditioning case 140.

The temperature-adjusting door 145 is mounted between the evaporator 141 and the heater core 142 and regulates the degree of opening of a warm air passageway passing the heater core 142 and the degree of opening of a cold air passageway bypassing the heater core 142 to control temperature of discharged air. A plurality of mode doors 146 are respectively mounted at the air outflow ports 144 to selectively open and close the air outflow ports 144 according to various air-conditioning modes.

Figure 4:
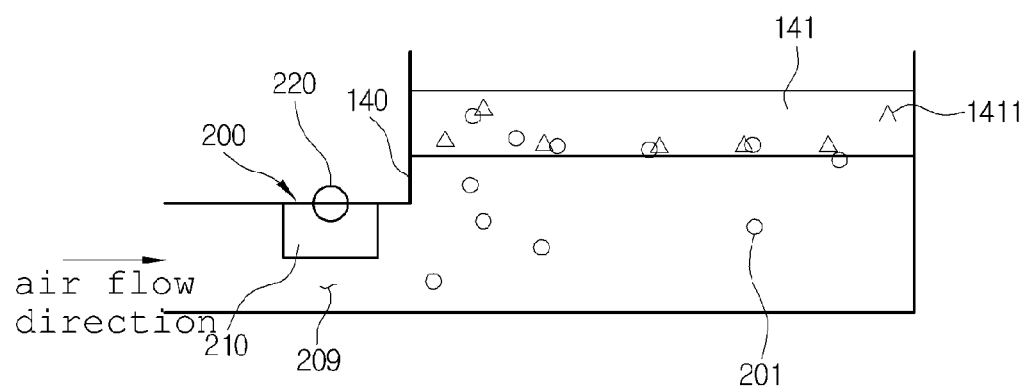
FIG. 4 is a brief diagram of a photocatalytic module of the air conditioner for the vehicle according to the first preferred embodiment of the present invention.
Figure 5:
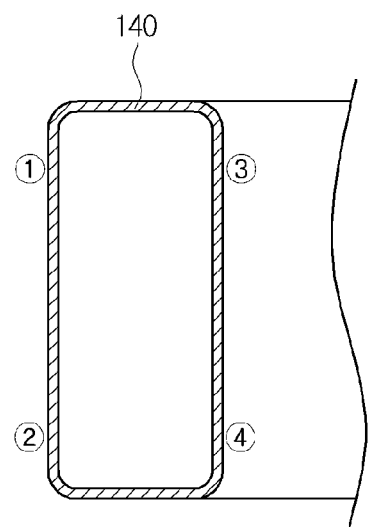
FIG. 5 is a sectional view showing a partial cross section of an air-conditioning case of the air conditioner for the vehicle according to the first preferred embodiment of the present invention.
Figure 6:
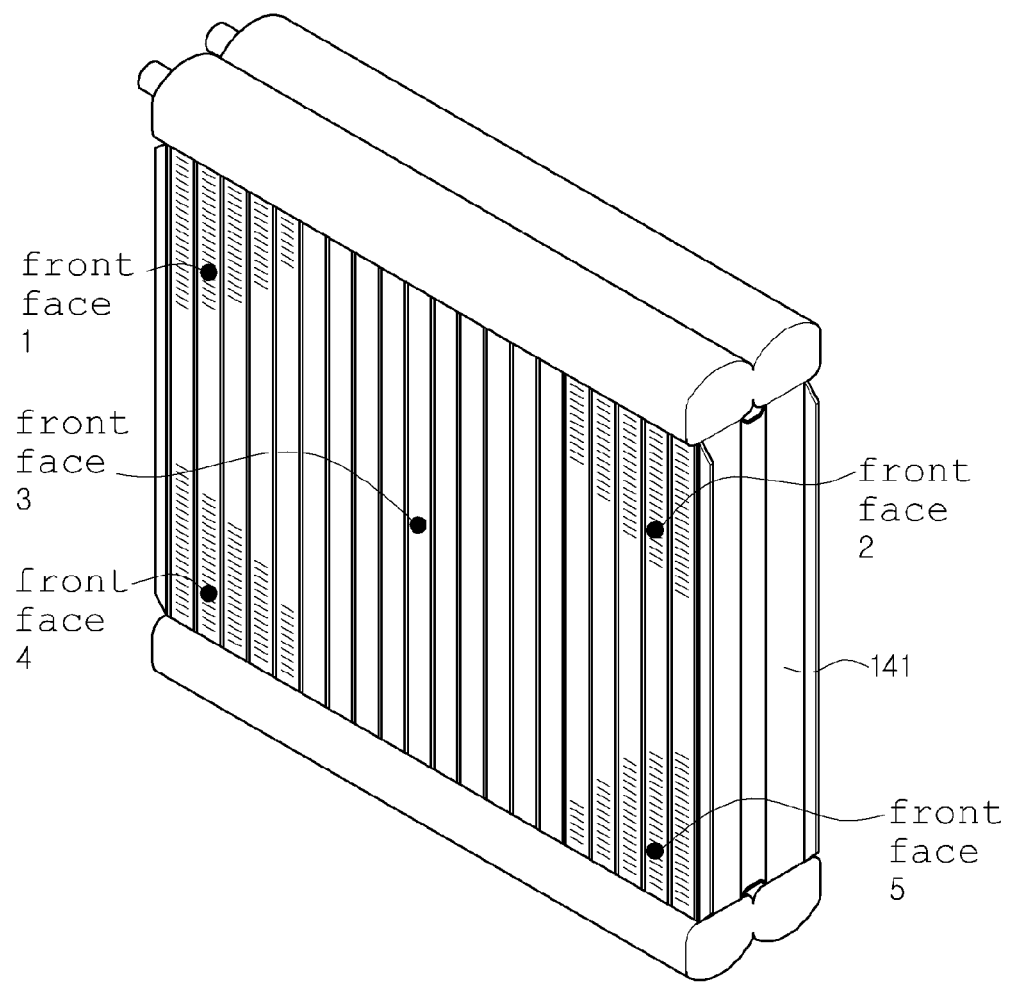
FIG. 6 is a perspective view showing a front face of an evaporator according to the first preferred embodiment of the present invention.
Figures 7, 8:
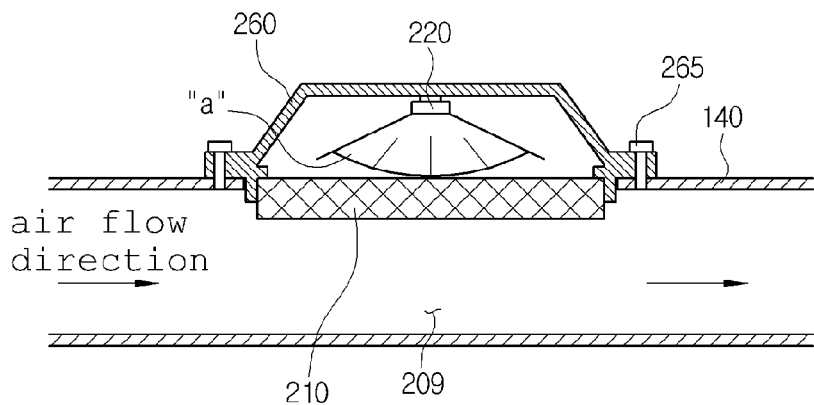
FIG. 7 is a graph showing a bacteria removing rate by a mounting position of the photocatalytic module according to the first preferred embodiment of the present invention.
FIG. 8 is an enlarged sectional view of the photocatalytic module of the air conditioner for the vehicle according to the first preferred embodiment of the present invention.
Figure 9:
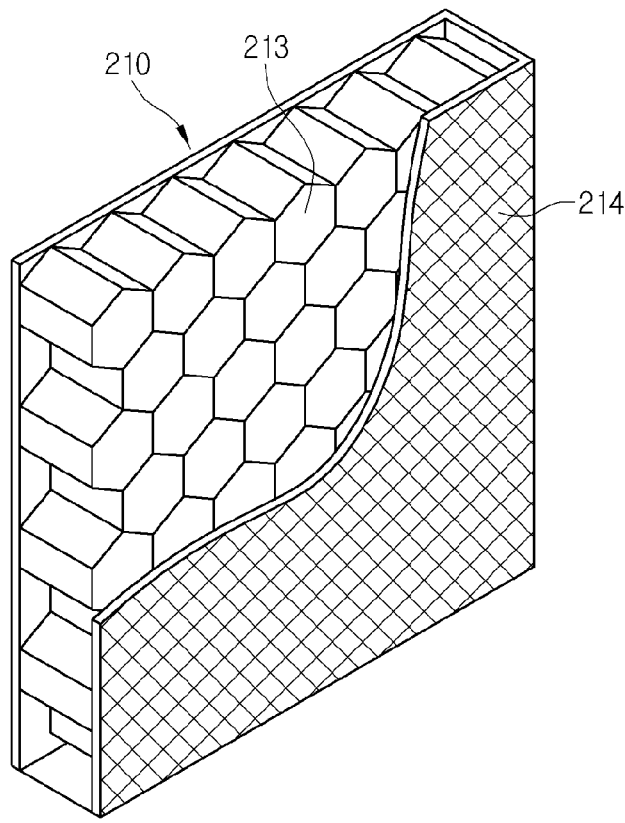
FIG. 9 is a perspective view of a catalyst part of the air conditioner for the vehicle according to the first preferred embodiment of the present invention.

FIG. 4 is a brief diagram of a photocatalytic module of the air conditioner for the vehicle according to the first preferred embodiment of the present invention, FIG. 5 is a sectional view showing a partial cross section of an air-conditioning case of the air conditioner for the vehicle according to the first preferred embodiment of the present invention, FIG. 6 is a perspective view showing a front face of an evaporator according to the first preferred embodiment of the present invention, FIG. 7 is a graph showing a bacteria removing rate by a mounting position of the photocatalytic module according to the first preferred embodiment of the present invention, FIG. 8 is an enlarged sectional view of the photocatalytic module of the air conditioner for the vehicle according to the first preferred embodiment of the present invention, and FIG. 9 is a perspective view of a catalyst part of the air conditioner for the vehicle according to the first preferred embodiment of the present invention.

Referring to FIGS. 4 to 9, the photocatalytic module 200 is disposed at one side of the air-conditioning case 140 and includes a catalyst part 210 and a light source part 220.

The photocatalytic module 200 has a structure that the catalyst part 210 and the light source part 220 are modulated into one. Therefore, the photocatalytic module 200 is easily attached and detached and conveniently maintained and repaired.

The catalyst part 210 causes a photocatalytic reaction by irradiated light to generate radicals 201. The catalyst part is arranged to supply the generated radicals 201 to the air passageway formed in inside the air-conditioning case 140. The catalyst part 210 contains carriers, such as ceramics, and materials with low air resistance in order to minimize decrease of air volume of the moving air passing the catalyst part 210.

The catalyst part 210 causes the photocatalytic reaction by light irradiated from the light source part 220 which will be described later, and pollutants introduced into the inside of the air-conditioning case 140 and bacteria, various pollutants and bad smells inside the evaporator 141 are removed by the oxidation process of the radicals 201 generated by the photocatalytic reaction.

At least one light source part 220 is served to irradiate UV light toward the catalyst part 210. When the photocatalytic carriers of the catalyst part 210 absorb light by the light source part 220, electrons in the valence band (VB) which is filled electrons absorb light energy and jump to the conduction band (CB) which is empty and has no electrons. A hole which is the empty space of the valence band oxidizes water molecules on the surface thereof so that the hole is restored to its original condition and the oxidized water molecules form OH radicals. Moreover, electrons excited to the conduction band are called 'excited electrons', and react with oxygen to generate hyperoxy radicals ($.O_2-$) with strong oxidizing power.

Compared with the structure to adsorb and deodorize polluted air containing bad smell, the structure of the photocatalytic module 200 that includes the catalyst part 210 and the light source part 220 to generate the radicals 201 by the photocatalytic reaction does not need replacement of the filter and can be used semipermanently through selection of kinds of the carriers or the proper on-off control of the light source part. That is, the photocatalytic module 200 according to the first preferred embodiment of the present invention has long lifespan.

The light source part 220 includes a light emitting diode (LED) radiating light of ultra violet-A (VUA) which has wavelength of less than 380 nm or light of ultra violet-C (UVC). The light source part 220 can solve the problems of mercury and effectively irradiate light with small electric power because the light source part 220 includes the LED. In this instance, the UVA is relatively low priced and effectively activates the photocatalytic reaction of the photocatalytic carriers. Moreover, the UVC is relatively high priced but can activate the photocatalytic reaction and carry out a bactericidal function to enhance sterilization efficiency.

The photocatalytic module 200 is disposed on the wall of one side of the air-conditioning case 140 to form a passing part 209 on a passageway of air. That is, the photocatalytic module 200 is mounted on the inner wall or a part of the center of the air passageway of the air-conditioning case 140 to minimize decrease of volume of the air flowing inside the air-conditioning case 140. The passing part 209 is an empty space of the air passageway of the air-conditioning case 140 which the photocatalytic module 200 does not occupy, so that the air volume can pass the passing part smoothly.

That is, the photocatalytic module 200 includes a module case 260 which is opened at one side and is closed at the other side to form a inner space part. The light source part 220 is connected to the inner space part of the module case 260, and the catalyst part 210 is connected to the opening part of the module case 260. The catalyst part 210 is mounted to get into the air-conditioning case 140. Through such a configuration, the photocatalytic module 200 can be easily mounted in the air-conditioning case 140.

The module case 260 surrounds the light source part 220 and the catalyst part 210 to embed the light source part 220 and the catalyst part 210 therein, and is detachably connected to the air-conditioning case 140. The module case 260 is disposed to communicate with inside the air-conditioning case so that the catalyst part 210 can come in contact with the air passageway. The module case 260 is screw-coupled with the air-conditioning case 140 through bolt, can be removably coupled with the air conditioning case 140 through other coupling structures. As described above, when the module case 260 is detachably connected to the air-conditioning case 140, it provide superior assemblability and mounting performance and easy maintenance.

The opening part of the module case 260 is connected to the outside of the air-conditioning case 140, and the light source part 220 is arranged on the outer face of the air-conditioning case 140. The catalyst part 210 is arranged inside the air-conditioning case 140. Therefore, when the photocatalytic module 200 is inserted into the air-conditioning case to the minimum, resistance of air flow path inside the air-conditioning case 140 is minimized and the radicals 201 generated by the catalyst part 210 exposed to the inside of the air-conditioning case 140 is supplied to the evaporator 141 smoothly.

Referring to FIG. 9, it is preferable that the catalyst part 210 have a honeycomb body 213 which is filled with catalyst. The catalyst part 210 may have a mesh-shaped case 214 and the honeycomb body 213 disposed inside the case 214, and the honeycomb body 213 may be filled with photocatalytic carriers. Through the above-mentioned configuration, resistance of the air passing through the catalyst part 210 is minimized and decrease of air volume is also minimized.

The photocatalytic module 200 is arranged on the wall surface of the air-conditioning case 140 at the upstream side of the evaporator 141 in an air flow direction. The photocatalytic module 200 is formed on the air passageway inside the air-conditioning case 140 at the upstream side of the evaporator 141. Alternatively, the photocatalytic module 200 may be disposed on an air blowing duct which connects the air blower 110 and the air-conditioning case 140 with each other, or may be arranged inside the air blower 110.

Because the photocatalytic module 200 is arranged at the upstream side of the evaporator 141, the radicals 201 generated from the photocatalytic module 200 move toward the evaporator 141 together with the moving air so as to remove odor-causing materials 1411, such as microorganisms and harmful gases, existing in the evaporator 141.

Finally, compared with the structure which collects the odor-causing materials 1411 of the evaporator 141 at the downstream side of the evaporator 141, the air conditioner 100 according to the first preferred embodiment of the present invention fundamentally removes the odor-causing materials 1411 of the evaporator 141 by supplying the radicals 201 to the evaporator 141 at the upstream side of the evaporator 141 so as to remove bad smells more effectively and make the replacement period of the filter shorter.

The air-conditioning case 140 includes a passageway converting part to convert a flow direction of the air at the upstream side of the evaporator 141. The passageway converting part is a section where the air blown from the air blower 110 changes the flow direction at 90 degrees, and the photocatalytic module 200 is mounted at the passageway converting part. In more detail, the photocatalytic module 200 is arranged on the surface of the inner wall of a curved part of the passageway converting part that has relatively shorter air flow path and is more adjacent to the evaporator 141.

FIG. 5 is a sectional view that the air-conditioning case 140 is cut at a front end of the passageway converting part. In FIG. 5, the photocatalytic module 200 may be arranged at the position of No. 1, No. 2, No. 3 or No. 4. In this instance, the surfaces of the inner wall of the curved part where the air passageway is relatively shorter and is more adjacent to the evaporator 141 are the position of No. 3 and the position of No. 4. Preferably, the photocatalytic module 200 is arranged at a lower area, out of the passageway converting part of the air-conditioning case 140, in the height direction of the air-conditioning case 140. The lower areas in the height direction are the position of No. 2 and the position of No. 4. Finally, it is the most preferable that the photocatalytic module 200 be arranged on the surface of the inner wall of the curved part of the passageway converting part and at the lower area in the height direction, namely, at the position of No. 4.

Referring to FIG. 7, when the photocatalytic module 200 is arranged at the positions of Nos. 1 to 4, bacteria removal rates of the front face part of the evaporator at each of the positions where the photocatalytic module 200 is mounted were measured. In this instance, as shown in FIG. 6, the measurement positions of the evaporator were five, namely, the front face 1, the front face 2, the front face 3, the front face 4 and the front face 5. As a result of an experiment, as shown in FIG. 7, when the photocatalytic module 200 was mounted at the position of No. 4, the bacterial removal rate of the evaporator was the highest.

Figure 10:
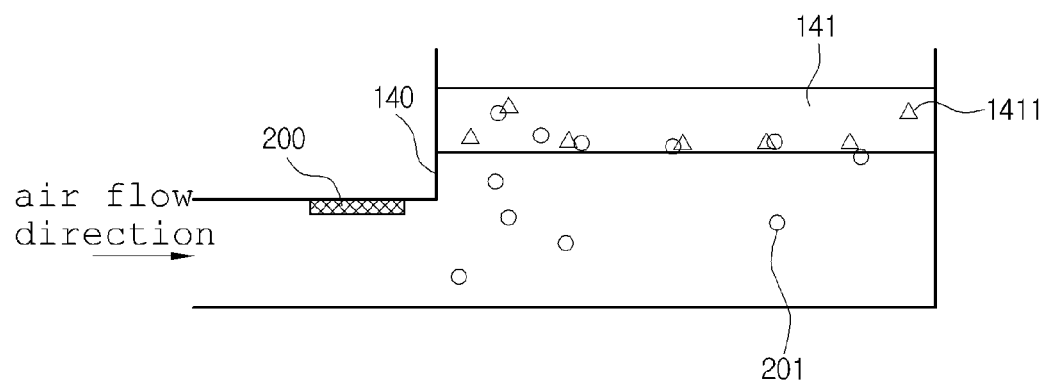
FIG. 10 is a view showing an arrangement direction of the catalyst part according to the first preferred embodiment of the present invention.

FIG. 10 is a view showing an arrangement direction of the catalyst part according to the first preferred embodiment of the present invention. Referring to FIG. 10, the catalyst part 210 includes a flat part which is arranged side by side with the air flow direction inside the air-conditioning case 140. That is, the catalyst part 210 includes the flat part which is formed in a plate type of a predetermined thickness. The flat part is arranged side by side with the air flow direction inside the air-conditioning case 140. Such a structure makes the catalyst part 210 minimize air flow resistance inside the air-conditioning case 140.

Figure 11:
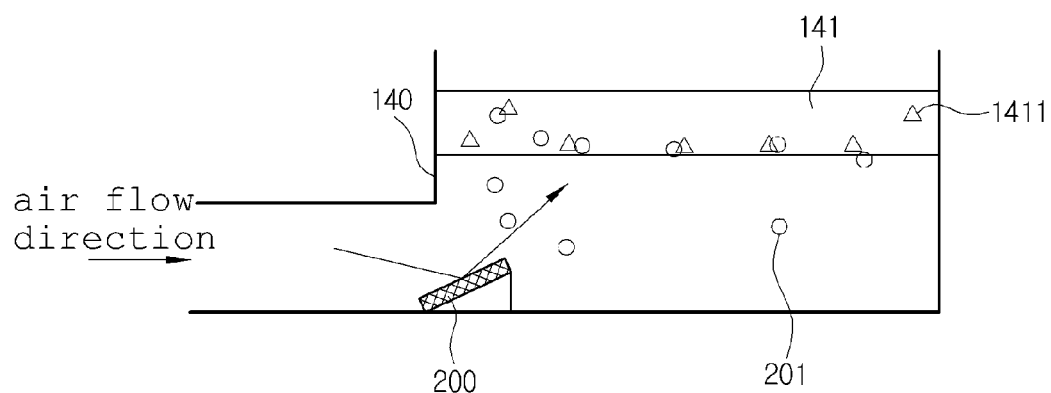
FIG. 11 is a view showing an arrangement direction of the catalyst part according to a modification of FIG. 10.

In the meantime, FIG. 11 is a view showing an arrangement direction of the catalyst part according to a modification of FIG. 10. Referring to FIG. 11, the catalyst part 210 includes a plane part which is arranged to be inclined to the air flow direction inside the air-conditioning case 140. That is, the catalyst part 210 has the plane part which is formed in a plate type of a predetermined thickness, and the plane part is arranged to be inclined to the air flow direction. In this instance, the inclination direction of the catalyst part 210 is formed in such a way that the moving air is guided toward the evaporator 141 by the catalyst part 210. As described above, because the inclination direction of the catalyst part 210 becomes a direction of the passageway converting part, it provides the function to generate radicals and the function to guide the air flow from the passageway converting part to the evaporator.

Figure 12:
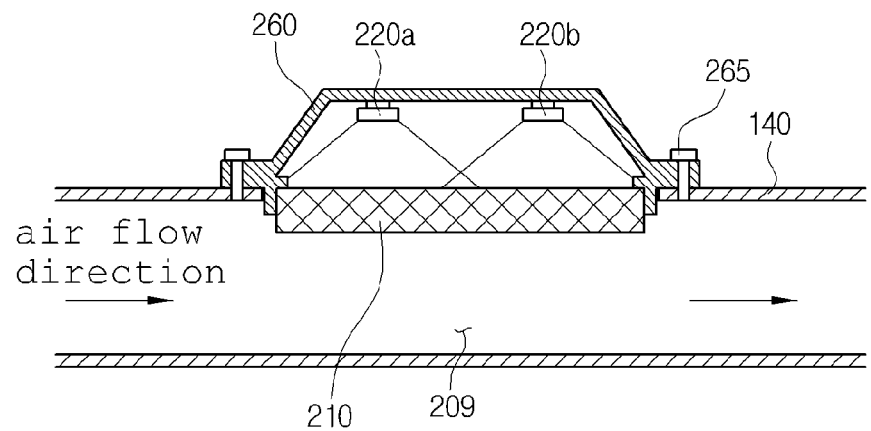
FIG. 12 is an enlarged sectional view of a photocatalytic module according to a modification of FIG. 8.

FIG. 12 is an enlarged sectional view of a photocatalytic module according to a modification of FIG. 8. Referring to FIG. 12, a plurality of the light source part 220 are arranged side by side about the catalyst part 210 inside the module case 260. In this embodiment, a pair of the light source parts 220 are disposed, but three or more light source parts 220 may be disposed. Preferably, in FIG. 5, the light source parts 220 are respectively mounted at the positions of No. 3 and No. 4. Through the above structure, light radiated from the plurality of the light source part 220 promotes the reaction of the catalyst part 210 to generate more radicals.

Figure 13:
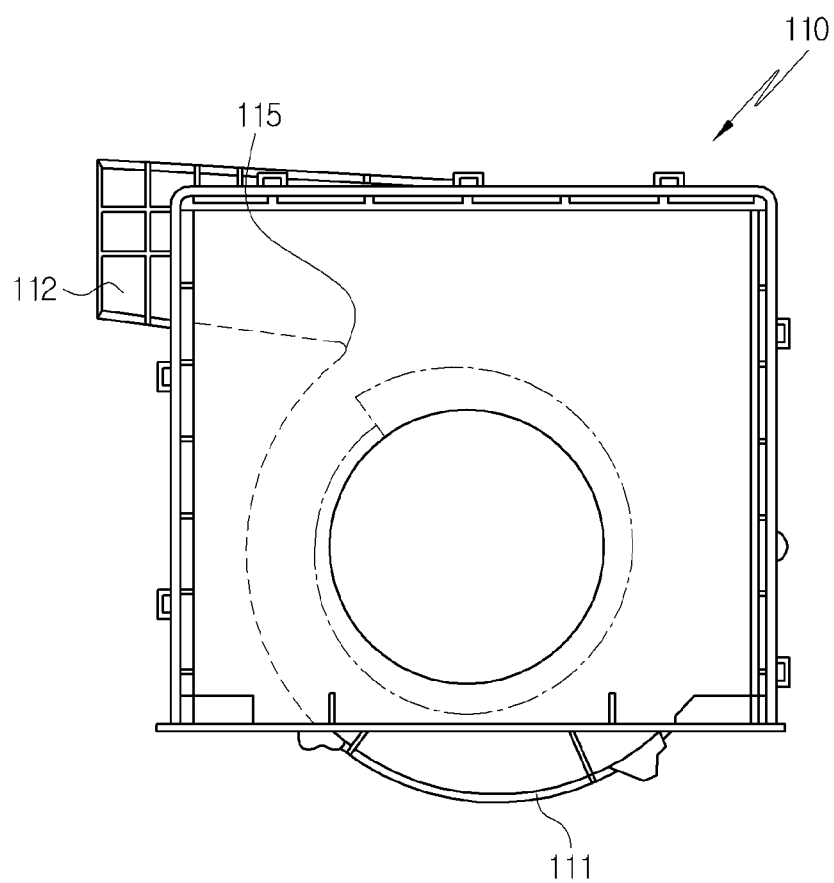
FIG. 13 is a top view of a scroll part showing cutoff of an air blower according to a second preferred embodiment of the present invention.
Figure 14:
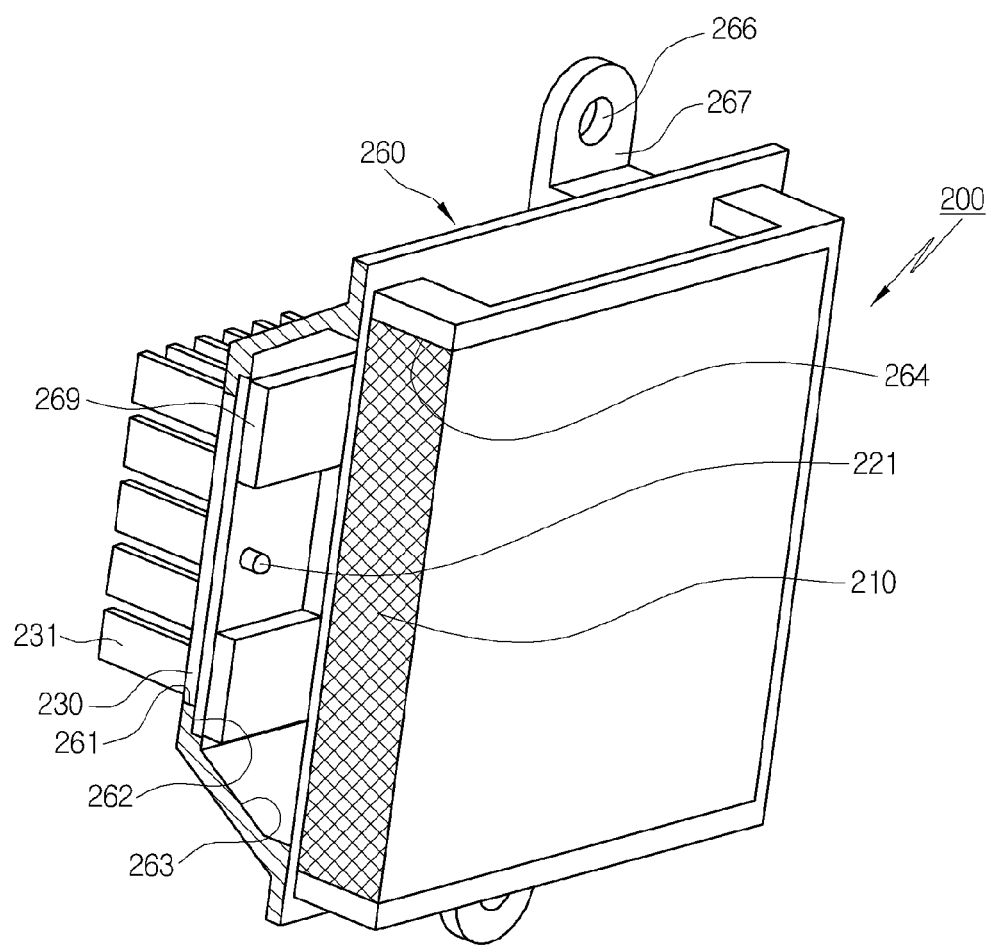
FIG. 14 is a perspective view showing a photocatalytic module according to the second preferred embodiment of the present invention.
Figure 15:
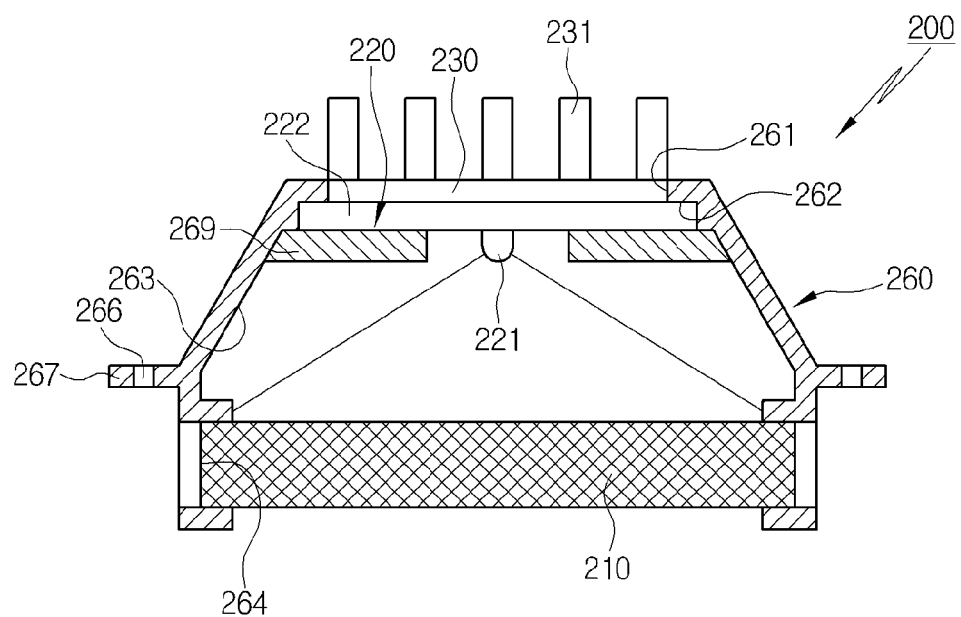
FIG. 15 is a sectional view showing the photocatalytic module according to the second preferred embodiment of the present invention.

FIG. 13 is a top view of a scroll part showing cutoff of an air blower according to a second preferred embodiment of the present invention, FIG. 14 is a perspective view showing a photocatalytic module according to the second preferred embodiment of the present invention, and FIG. 15 is a sectional view showing the photocatalytic module according to the second preferred embodiment of the present invention.

In description of the second preferred embodiment, the same components as the first preferred embodiment have the same reference numerals as the first preferred embodiment, and their detailed description will be omitted.

As shown in FIGS. 2 and 13 to 15, the air conditioner 100 for the vehicle with the photocatalytic module according to the second preferred embodiment of the present invention includes an air-conditioning case 140, an evaporator 141, a heater core 142, an air blower 110, a temperature-adjusting door 145, a plurality of mode doors 146 and a photocatalytic module 200.

The air blower 110 includes: an inlet duct which has an inside air inlet 121, an outside air inlet 122 and an inside and outside air converting door 123; and a scroll case which is connected below the inlet duct and on which a blast fan 135 is mounted. FIG. 13 is a top view of the scroll case in a state where the inlet duct is separated from the scroll case. As shown in FIG. 13, the blast fan 135 is arranged on a scroll part 111 to be able to rotate, and an exit part 112 is formed to communicate with the scroll part 111 and is extended in a direction of an exit of the scroll part 111. Therefore, a cutoff 115 is formed at a boundary between a scroll start part of the scroll part 111 and the exit part 112.

The photocatalytic module 200 includes a catalyst part 210, a light source part 220, a module case 260 and a radiation part 230. The catalyst part 210 and the light source part 220 of the photocatalytic module 200 are all disposed inside the module case 260 and are modulated into one. Therefore, the photocatalytic module 200 is easily mounted in the air-conditioning case 140, is easily attached and detached and conveniently maintained and repaired.

The radiation part 230 is disposed at one side of the light source part 220 to release heat generated from the light source part 220. The radiation part 230 prevents overheating of the light source part 220 having an LED 221 so as to prevent deterioration in performance of the photocatalytic module 200. If temperature of the photocatalytic module 200 increases, the intensity of radiation of the light source part 220 decreases, and hence, a production rate of hyperoxy radicals is reduced. Therefore, the radiation part 230 restrains increase of temperature of the photocatalytic module 200 and can keep the production rate of the hyperoxy radicals at a predetermined level.

The light source part 220 includes an LED 221 and an LED panel 222 for fixing the LED 221. In this instance, the radiation part 230 includes a plurality of radiation fins 231. The radiation fins 231 are connected to get in contact with the opposite side of the LED panel 222 on which the LED 221 is formed. The radiation fins 231 are formed to protrude from the side opposed to the side which gets in contact with the LED panel 222 in order to increase a heat-exchange area with the outside air to enhance a radiation effect. Moreover, the radiation part 230 may get in direct contact with the LED panel 222 in order to radiate heat generated from the LED 221 more effectively.

The module case which surrounds the light source part 220 and the catalyst part 210 therein includes an opening part 261, a stepped part 262, an inclined part 263 and a catalyst part recess 264. The opening part 261 is formed at one side of the module case 260, and the radiation part 230 is inserted and joined into the opening part 261. The stepped part 262 protrudes from the opening part 261 to be stepped inwardly and supports the LED panel 222. The catalyst part recess 264 is formed at the other side of the module case 260 and receives the catalyst part 210. The inclined part 263 guides light radiated from the light source part 220 toward the catalyst part 210 so that the light is concentrated at the catalyst part 210 to increase a catalyst reaction amount. The module case 260 has a bracket 267 having a coupling hole 266 to be coupled to the wall surface of the air-conditioning case 140.

Figure 16:
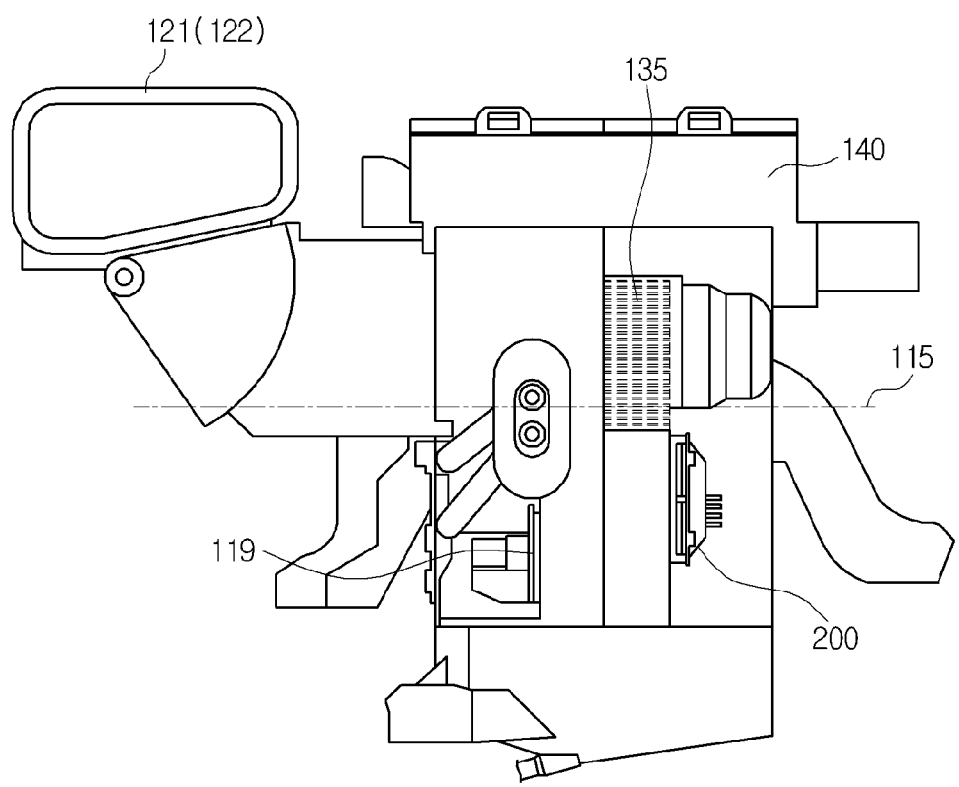
FIG. 16 is a front view showing a state where the photocatalytic module is arranged on the center-mounting type air conditioner according to the second preferred embodiment of the present invention.
Figure 17:
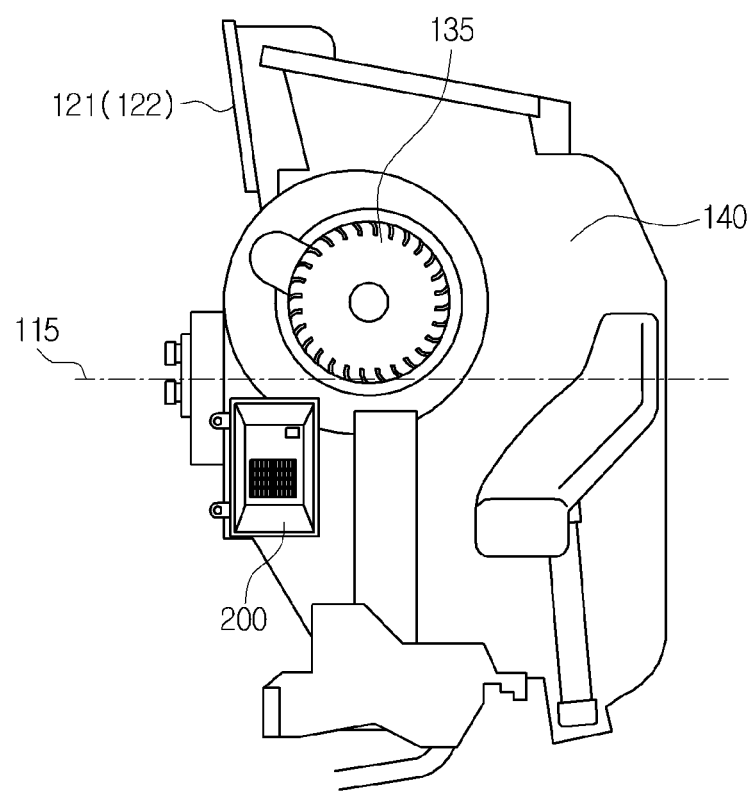
FIG. 17 is a side view showing the state where the photocatalytic module is arranged on the center-mounting type air conditioner according to the second preferred embodiment of the present invention.

FIG. 16 is a front view showing a state where the photocatalytic module is arranged on the center-mounting type air conditioner according to the second preferred embodiment of the present invention, and FIG. 17 is a side view showing the state where the photocatalytic module is arranged on the center-mounting type air conditioner according to the second preferred embodiment of the present invention.

In FIG. 16, the horizontal direction means an "axial direction of the blast fan" and a "width direction of the air conditioner", and the vertical direction means a "radial direction of the blast fan". Additionally, in FIG. 17, the left direction means a "front side" and the right direction means a "rear side". In addition, in FIGS. 16 and 17, the part indicated by the two point chain line is a horizontal extension line of the cutoff.

Referring to FIGS. 16 and 17, the photocatalytic module 200 is arranged in the opposite direction to the inside air and outside air inlets 121 and 122 of the air blower 110 in the air flow direction. That is, the photocatalytic module 200 is located in the opposite direction to the inside air and outside air inlets 121 and 122 in the width direction of the air conditioner. The air introduced through the inside air and outside air inlets 121 and 122 flows in the horizontal direction, namely, in parallel with the axial direction of the blast fan 135, after, flows in the vertical direction by rotation of the blast fan 135, namely, in the radial direction of the blast fan 135, and then, flows into the air-conditioning case 140.

In this instance, because the photocatalytic module 200 is disposed in the opposite direction to the inside air and outside air inlets 121 and 122, a air volume introduced through the inside air and outside air inlets 121 and 122 and passing the photocatalytic module 200 is relatively increased. Therefore, the increase of the flow rate of the air passing the catalyst part 210 enhances sterilization and deodorization performance of the photocatalytic module 200.

Moreover, the photocatalytic module 200 is arranged downstream side the cutoff 115, which is the boundary between the scroll start part and the exit part of the air blower 110, in the air flow direction. That is, the photocatalytic module 200 is located below the extension line of the cut off 115 in the vertical direction of the air conditioner, namely, is located at a part where the air passes the cutoff 115. Therefore, the air conditioner according to the present invention can reduce resistance to the cutoff 115 to solve noise problem. In a case that the photocatalytic module 200 is arranged at the upstream side of the cutoff 115 in the air flow direction, resistance to the cutoff 115 is increased by the photocatalytic module 200, and it causes increase of noise. Therefore, when the photocatalytic module 200 is optimized in arrangement, the noise problem can be solved.

The air conditioner for the vehicle according to the second preferred embodiment of the present invention is the center-mounting type air conditioner in which the evaporator 141, the heater core 142 and the air blower 110 are formed integrally in the air-conditioning case. The center-mounting type air conditioner has a problem in that resistance is suddenly increased at the cutoff part 115 and increases noise. Therefore, the photocatalytic module 200 is located downstream side the cutoff 115 in the air flow direction in order to solve the noise problem.

Furthermore, as described above, in case of the photocatalytic module 200, the catalyst part 210 and the light source part 220 are embedded in the single module case 260 in a state where the catalyst part 210 and the light source part 220 are arranged in order. In this instance, the module case 260 is connected to the air-conditioning case 140 to be side by side with the arrangement direction of the catalyst part 210 and the light source part 220. When a bolt, etc. is screw-coupled to the coupling hole 266 of the bracket 267 of the module case 260, the photocatalytic module 200 can be connected to the air-conditioning case 140.

As shown in FIG. 16, the connection direction of the module case 260 is side by side with the axial direction of the blast fan 135 of the air blower 110. The air introduced through the inside air and outside air inlets 121 and 122 passes the cutoff 115 while flowing in the radial direction by rotation of the blast fan 135, and then, passes the catalyst part 210 of the photocatalytic module 200. The connection direction of the catalyst part 210 is side by side with the axial direction of the blast fan 135 so that the volume of the air passing the catalyst part 210 can be increased relatively.

Figure 18:
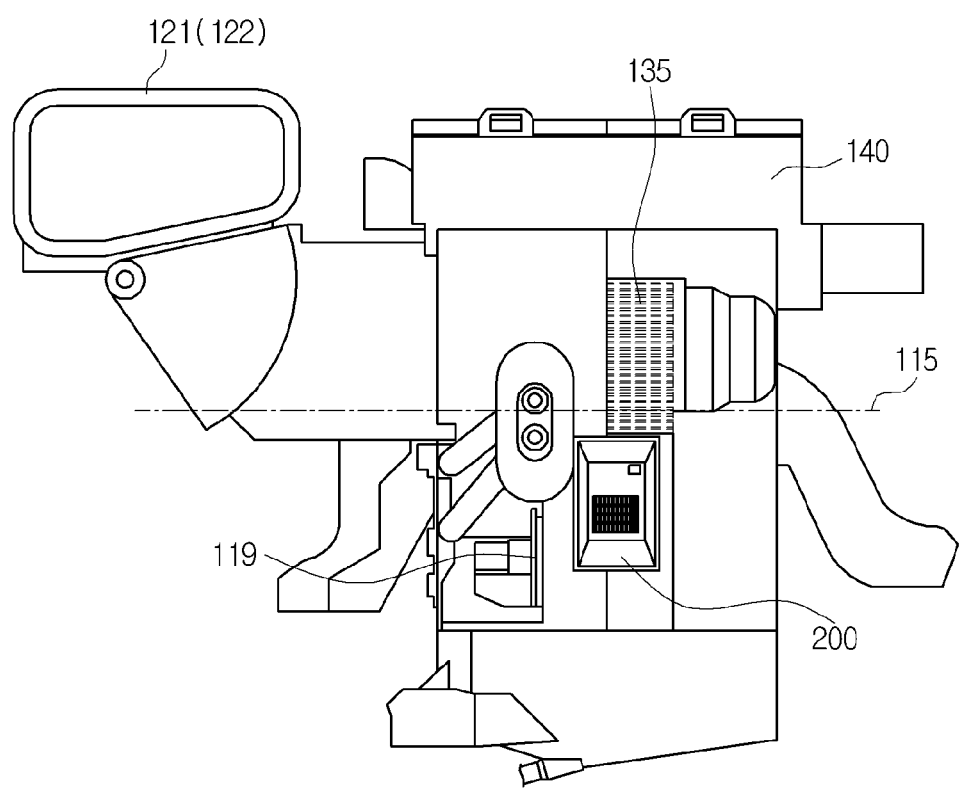
FIG. 18 is a front view showing a state where the photocatalytic module is arranged on the center-mounting type air conditioner according to a modification of FIG. 16.

In the meantime, FIG. 18 is a front view showing a state where the photocatalytic module is arranged on the center-mounting type air conditioner according to a modification of FIG. 16. Referring to FIG. 18, the module case 260 may be formed on an extension of the blast fan 135 of the air blower 110 in the radial direction. The air introduced through the inside air and outside air inlets 121 and 122 passes the cutoff 115 while flowing in the radial direction by rotation of the blast fan 135, and then, passes the catalyst part 210 of the photocatalytic module 200. Because the catalyst part 210 is arranged on the extension of the blast fan 135 of the air blower 110 in the radial direction, resistance of the air passing the catalyst part 210 can be decreased relatively.

Moreover, the photocatalytic module 200 is arranged oppositely to a resistor 119 in the air flow direction. That is, the photocatalytic module 200 is arranged in the opposite direction to the resistor 119 in the width direction of the air conditioner. The resistor 119 is mounted to control electricity supplied to the air blower 110. The resistor 119 serves to control a rotational speed of a blower motor, and is mounted inside an outlet of the scroll case of the air blower 110. If the resistor 119 and the photocatalytic module 200 are located at the same side, it increases resistance applied to one side to cause increase of noise and deterioration in performance. Therefore, the photocatalytic module 200 arranged at the optimized location can prevent the noise problem and the deterioration in performance.

Figure 19:
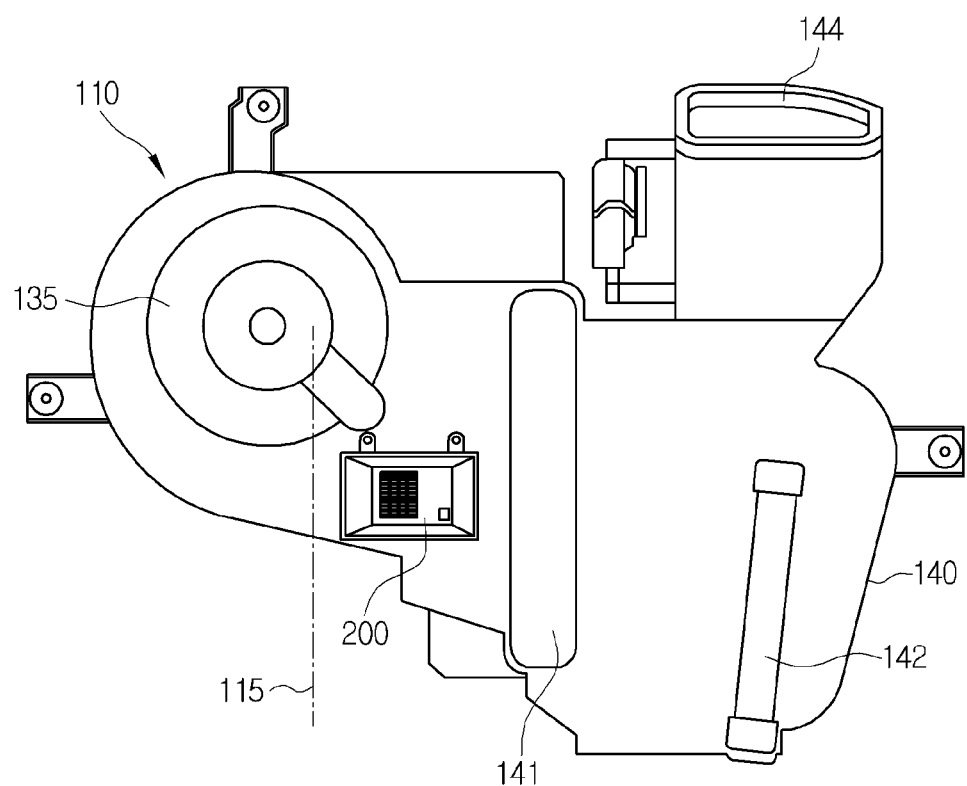
FIG. 19 is a view showing a state where the photocatalytic module is arranged on a rear air conditioner according to a modification of FIG. 17.

Meanwhile, FIG. 19 is a view showing a state where the photocatalytic module is arranged on a rear air conditioner according to a modification of FIG. 17. As shown in FIG. 19, the arrangement of the photocatalytic module 200 described in the above preferred embodiments can be applied to the rear air conditioner in the same way. That is, the structure that the photocatalytic module is arranged in the opposite direction to the inside air and outside air inlets, the structure that the photocatalytic module is arranged at the part where the air passes the cutoff and the structure that the photocatalytic module is arranged in the opposite direction to the resistor can be applied not only to the center-mounting type air conditioner and the semi-center type air conditioner but also to the rear air conditioner in the same way.

Figure 20:
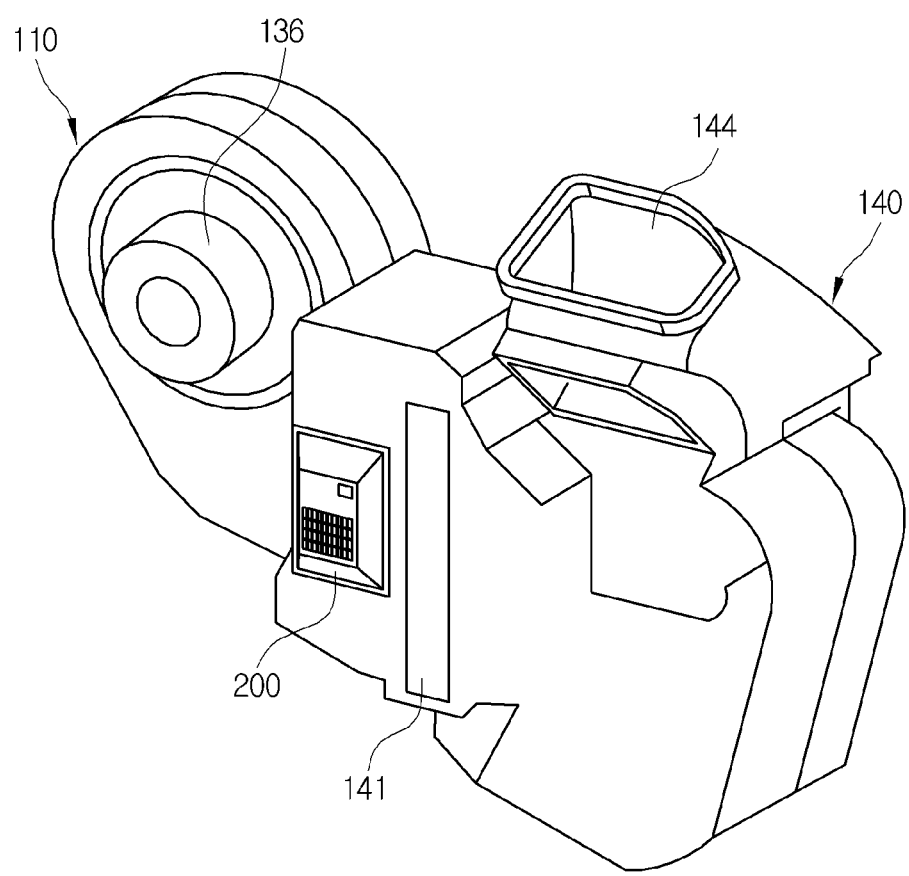
FIG. 20 is a perspective view showing a state where the photocatalytic module is arranged on a rear air conditioner according to a third preferred embodiment of the present invention.
Figure 21:
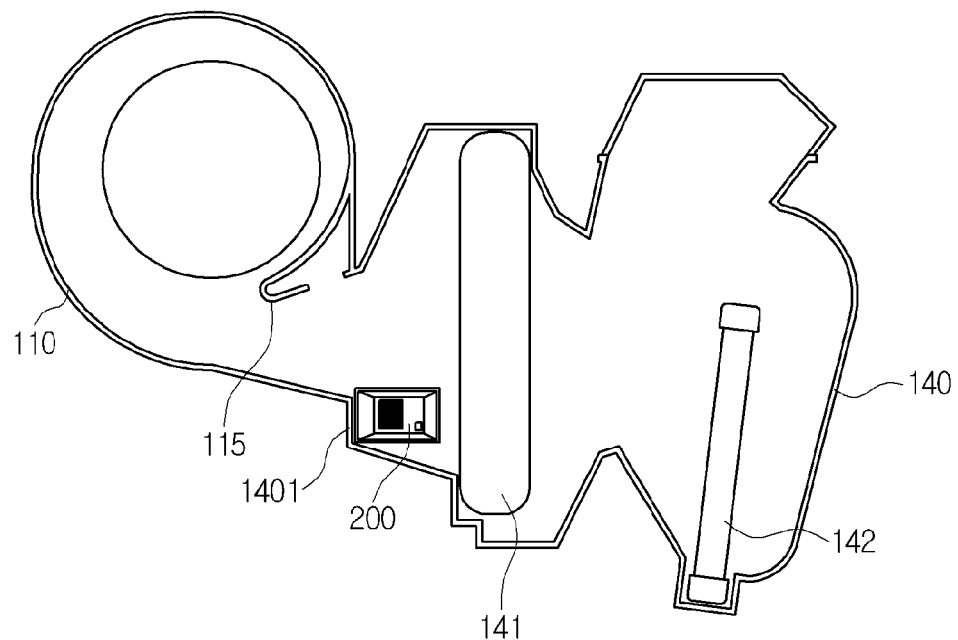
FIG. 21 is a sectional view showing the state where the photocatalytic module is arranged on the rear air conditioner according to the third preferred embodiment of the present invention.

FIG. 20 is a perspective view showing a state where the photocatalytic module is arranged on a rear air conditioner according to a third preferred embodiment of the present invention, and FIG. 21 is a sectional view showing the state where the photocatalytic module is arranged on the rear air conditioner according to the third preferred embodiment of the present invention.

In the third preferred embodiment, the same components as the first preferred embodiment have the same reference numerals as the first preferred embodiment, and their detailed description will be omitted.

Hereinafter, in FIG. 21, the direction from the left to the right means the "air flow direction".

Referring to FIGS. 20 and 21, the photocatalytic module 200 according to the third preferred embodiment of the present invention is arranged adjacent to the evaporator 141 than a blast fan (135) on the passageway which passes the cutoff 115 of the air blower 110 in the air flow direction. That is, the photocatalytic module 200 is located between the blast fan 135 and the evaporator 141, and is arrange as close as possible to the evaporator 141 on the passageway which passes the cutoff 115.

Therefore, because the photocatalytic module 200 is located at a smooth air flow part between the blast fan 135 and the evaporator 141, the air conditioner according to the present invention can sufficiently secure the volume of air passing the catalyst part 210 to enhance sterilization and deodorization performance and reduce resistance applied to the cutoff 115 to solve the noise problem. Furthermore, because the photocatalytic module 200 is arranged adjacent to the evaporator 141, the air conditioner according to the present invention can maximize sterilization and deodorization effects of the evaporator 141.

The rear air conditioner according to the third preferred embodiment of the present invention includes the air blower 110 and the evaporator 141 which are formed integrally in the air-conditioning case 140 and is mounted at the rear seat of the vehicle. In the rear air conditioner, because the air flow is smooth between the blast fan 135 and the evaporator 141, the photocatalytic module 200 is located between the blast fan 135 and the evaporator 141 to increase catalytic reaction of the photocatalytic module 200.

More preferably, the photocatalytic module 200 is arranged lower side of the evaporator 141 in the vertical direction. That is, the photocatalytic module 200 is arranged at the lower part in the vertical direction in the state where the evaporator 141 is mounted inside the air-conditioning case 140. Therefore, because the photocatalytic module 200 is located lower side of the evaporator 141 where a relatively large amount of condensate is formed to discharge radicals to the lower end of the evaporator 141, the air conditioner according to the present invention can concentrically deodorize and sterilize at the lower end of the evaporator 141 where microorganisms propagate well in order to maximize catalyst performance.

The inventor of the present invention found the problem caused from that the condensate water of the evaporator 141 is concentrated on the downstream direction by weight, and created this structure that the location of the photocatalytic module 200 is limited. Therefore, it is not a simple change in design and the present invention shows different effects in sterilization of the evaporator on which propagation of microorganisms is concentrated according to critical points of the location range of the photocatalytic module 200.

Additionally, the air-conditioning case 140 has a stepped wall 1401 which extends downwardly so that the passageway that introduced inflowing air through the air blower 110 toward the evaporator 141 is expanded in the vertical direction. In this instance, the photocatalytic module 200 is located on the stepped wall 1401 formed vertically. Finally, the photocatalytic module 200 is arranged lower side of the evaporator 141 in the vertical direction and is located on the stepped wall 1401 in such a way that the vertical height is received in the stepped wall 1401, so that the photocatalytic module 200 can minimize resistance with little influence on the air flow.

Figure 22:
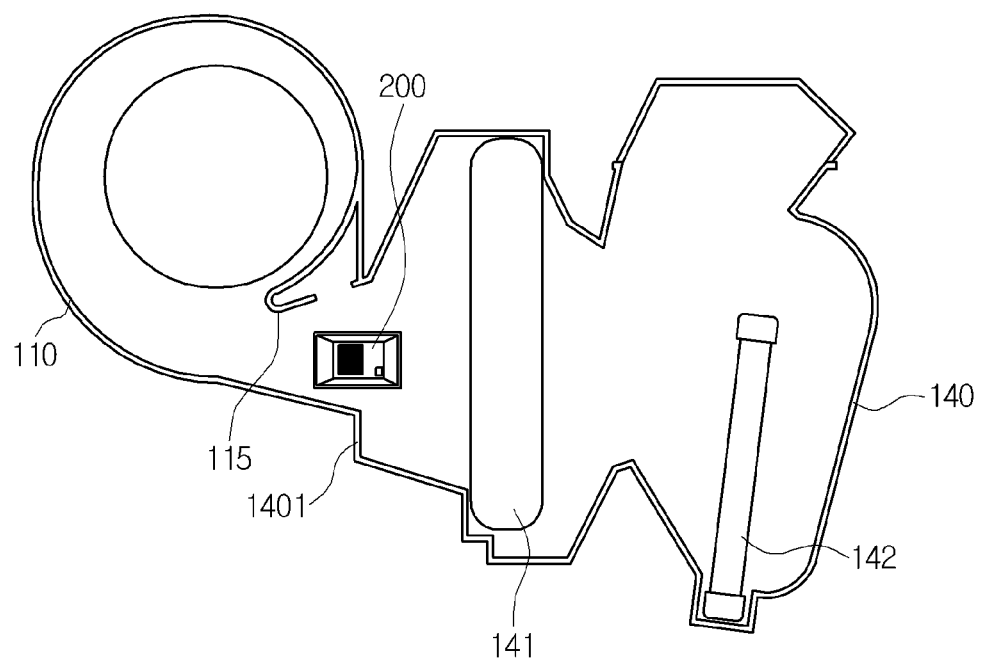
FIG. 22 is a sectional view showing a state where the photocatalytic module is arranged on the rear air conditioner according to a modification of FIG. 21.

FIG. 22 is a sectional view showing a state where the photocatalytic module is arranged on the rear air conditioner according to a modification of FIG. 21. As shown in FIG. 22, the photocatalytic module 200 may be located upper than the stepped wall 1401 in the vertical direction. That is, the photocatalytic module 200 is arranged lower side of the evaporator 141 in the vertical length direction and is also arranged above the uppermost end of the stepped wall 1401. Finally, the photocatalytic module 200 is located between the stepped wall 1401 and center of the evaporator 141 in the vertical length direction. Therefore, the photocatalytic module is located at the central part of the passageway of the air blown from the air blower 110 toward the evaporator 141 in order to maximize the volume of the air passing the photocatalytic module 200 and maximize a generation amount of radicals.

Figure 23:
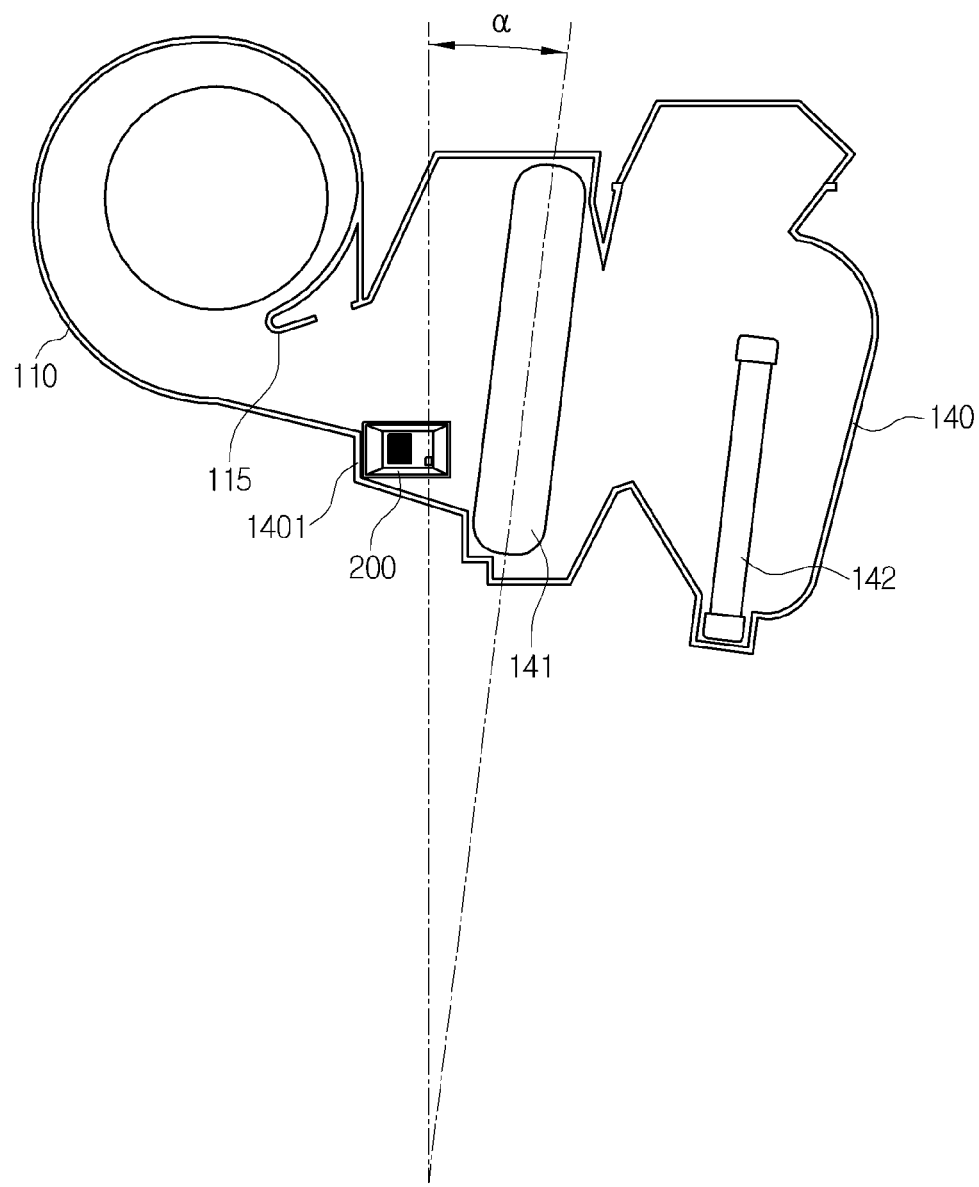
FIG. 23 is a sectional view showing a state where the photocatalytic module and the evaporator are arranged on the rear air conditioner according to a modification of FIG. 21.

Moreover, FIG. 23 is a sectional view showing a state where the photocatalytic module and the evaporator are arranged on the rear air conditioner according to a modification of FIG. 21. Referring to FIG. 23, the evaporator 141 is arranged to be inclined to the photocatalytic module 200. That is, the evaporator 141 and the photocatalytic module 200 are arranged to be inclined at a predetermined angle (α). In this instance, the photocatalytic module 200 is arranged lower side of the evaporator in the vertical length direction. Because the evaporator 141 is arranged to be inclined, the condensate water can be drained down more smoothly, and the photocatalytic module 200 located lower side of the evaporator 141 concentrically discharges radicals toward the lower part of the evaporator 141 in order to improve sterilization and deodorization effects of the evaporator 141.

Figure 24:
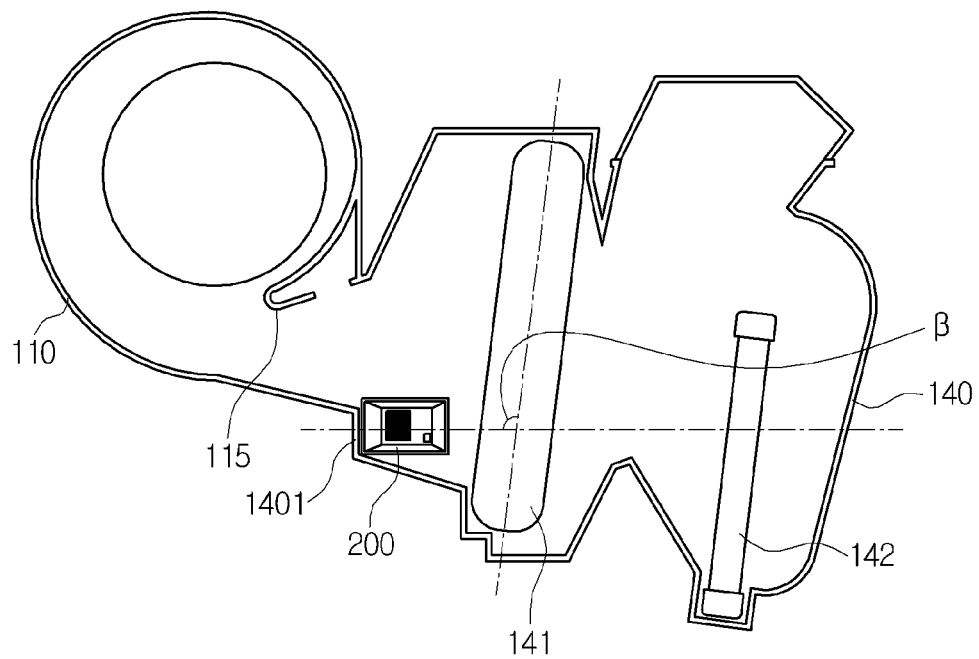
FIG. 24 is a sectional view showing an arrangement structure between the photocatalytic module and the evaporator according to FIG. 23.

In more detail, as shown in FIG. 24, a gradient (β) between a horizontal axis of the photocatalytic module 200 and a vertical axis of the evaporator 141 is more than 90 degrees. That is, the evaporator 141 is mounted to be inclined to the photocatalytic module 200 in order to make drain of the condensate water easy and maximize a synergy effect because the radicals on the front and back of the evaporator 141 are discharged out.

As described above, while the present invention has been shown and described with reference to the example embodiments illustrated in the drawings, it will be understood by those of ordinary skill in the art that the above embodiments of the present invention are all exemplified and various changes and equivalences may be made therein without departing from the technical idea of the present invention. Therefore, it would be understood that the technical and protective scope of the present invention shall be defined by the technical idea as defined by the following claims.

The invention claimed is:

1. An air conditioner for a vehicle with a photocatalytic module which includes: an air-conditioning case having an air inflow port formed at an entrance side, air outflow ports formed at an exit side and an air passageway formed inside the air-conditioning case; an evaporator mounted in the air passageway of the air-conditioning case; and an air blower for blowing inside air of the air-conditioning case, the air conditioner comprising:

a photocatalytic module disposed at one side of the air-conditioning case, wherein the photocatalytic module comprises:

a catalyst part which causes photocatalytic reaction by irradiated light to generate radicals; and at least one light source part for irradiating UV light toward the catalyst part;

wherein the photocatalytic module comprises a module case which is opened at one side and is closed at the other side to form an inner space part and surrounds the light source part and the catalyst part to embed the light source part and the catalyst part therein so that the light source part is connected to the inner space part of the module case and the catalyst part is connected to the opening part of the module case, thereby the module case is mounted to communicate with inside the air-conditioning case in such a way that the catalyst part gets in contact with the air passageway.

2. The air conditioner according to claim 1, wherein the photocatalytic module is mounted on a wall surface of the air-conditioning case at the upstream side of the evaporator in an air flow direction.

3. The air conditioner according to claim 2, wherein the air-conditioning case comprises a passageway converting part for converting a flow direction of the air at the upstream side of the evaporator, and the photocatalytic module is mounted on the passageway converting part.

4. The air conditioner according to claim 3, wherein the photocatalytic module is arranged on the surface of the inner wall of a curved part of the passageway converting part that has relatively shorter air flow path and is more adjacent to the evaporator.

5. The air conditioner according to claim 3, wherein the photocatalytic module is arranged at a lower area, out of the passageway converting part of the air-conditioning case, in the height direction of the air-conditioning case.

6. The air conditioner according to claim 1, wherein the module case is detachably connected to the air-conditioning case.

7. The air conditioner according to claim 1, wherein the catalyst part has a honeycomb body in which catalyst is put.

8. The air conditioner according to claim 1, wherein photocatalytic module comprises a plane part arranged side by side with the air flow direction inside the air-conditioning case.

9. The air conditioner according to claim 1, wherein the photocatalytic module comprises a plane part arranged to be inclined to the air flow direction inside the air-conditioning case.

10. The air conditioner according to claim 1, wherein a plurality of the light source parts are arranged side by side about the catalyst part inside the module case.

11. The air conditioner according to claim 1, wherein the photocatalytic module is arranged in the opposite direction to an inside air inlet and an outside air inlet of the air blower in the air flow direction.

12. The air conditioner according to claim 11, wherein the photocatalytic module is arranged below a cutoff of the air blower in the air flow direction.

13. The air conditioner according to claim 12, wherein the photocatalytic module has the structure that the light source part and the catalyst part are arranged in order inside the module case and the module case is connected to the air-conditioning case to be side by side with the arrangement direction of the light source part and the catalyst part, and wherein the connection direction of the module case is side by side with the axial direction of the blast fan of the air blower.

14. The air conditioner according to claim 12, wherein the photocatalytic module has the structure that the light source part and the catalyst part are arranged in order inside the module case and the module case is connected to the air-conditioning case to be side by side with the arrangement direction of the light source part and the catalyst part, and wherein the module case is disposed on a radial direction extension of a blast fan of the air blower.

15. The air conditioner according to claim 12, wherein the photocatalytic module is arrange oppositely to a resistor in the air flow direction, and the resistor is mounted to control electricity supplied to the air blower.

16. The air conditioner according to claim 11, wherein the air conditioner is a center-mounting type air conditioner in which the evaporator, the heater core and the air blower are formed integrally in the air-conditioning case.

17. The air conditioner according to claim 1, wherein the air conditioner is a rear air conditioner for vehicles in which the air blower and the evaporator are formed integrally inside the air-conditioning case and which is mounted at the rear seat of the vehicle, and wherein the photocatalytic module is arranged adjacent to the evaporator than a blast fan on the passageway which passes the cutoff of the air blower in the air flow direction.

18. The air conditioner according to claim 17, wherein the photocatalytic module is arranged lower side of the evaporator in the vertical length direction.

19. The air conditioner according to claim 18, wherein the air-conditioning case has a stepped wall which extends downwardly so that the passageway that introduced inflowing air through the air blower toward the evaporator is expanded in the vertical direction, and wherein the photocatalytic module is located on the stepped wall in the vertical direction.

20. The air conditioner according to claim 18, wherein the air-conditioning case has a stepped wall which extends downwardly so that the passageway that introduced inflowing air through the air blower toward the evaporator is expanded in the vertical direction, and wherein the photocatalytic module is located above the stepped wall in the vertical direction.

21. The air conditioner according to claim 18, wherein the evaporator is arranged to be inclined against the photocatalytic module.

22. The air conditioner according to claim 21, wherein a gradient (p) between a horizontal axis of the photocatalytic module and a vertical axis of the evaporator is more than 90 degrees.

23. The air conditioner according to claim 1, wherein the air conditioning case has an outer face that defines an opening, and wherein the module case is detachably connected to the outer face with the catalyst part extending across the opening and partially into the air passageway.

* * * * *